(12) United States Patent
Herbert

(10) Patent No.: US 6,251,415 B1
(45) Date of Patent: Jun. 26, 2001

(54) SOLVENT SYSTEM FOR PESTICIDE PRODUCTS

(75) Inventor: Richard M. Herbert, Medina, NY (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 08/958,420

(22) Filed: Oct. 27, 1997

(51) Int. Cl.$^7$ .................................................. A01N 25/02
(52) U.S. Cl. .......................... 424/405; 514/786; 514/789; 514/937; 514/939; 514/970
(58) Field of Search ..................... 424/405, 406; 514/786, 789, 919, 937–943, 970

(56) References Cited

U.S. PATENT DOCUMENTS

| | | | |
|---|---|---|---|
| 1,707,465 | * 4/1929 | Volck | 514/539 |
| 4,871,766 | * 10/1989 | Tguda et al. | 574/527 |
| 5,160,528 | 11/1992 | Chaudhuri et al. | 71/79 |
| 5,707,638 | * 1/1998 | Lösel et al. | 424/407 |
| 5,792,465 | * 8/1998 | Hagarty | 424/405 |

* cited by examiner

Primary Examiner—Neil S. Levy
(74) Attorney, Agent, or Firm—FMC Corporation

(57) ABSTRACT

A novel three component solvent system consisting of glyceryl triacetate, a substituted biphenyl, and a mixture of isoparafinic hydrocarbons is disclosed. The system is useful in the formulation of pesticides, and the use of the system to prepare emulsifiable concentrates and microemulsions is exemplified.

8 Claims, 1 Drawing Sheet

SOLVENT SYSTEM FOR PESTICIDE PRODUCTS

BACKGROUND OF THE INVENTION

The present invention relates to the general field of formulations of pesticides. In particular it relates to the development of a unique combination of solvents that affords more concentrated solutions of a number of pesticidally active materials, especially pyrethroids such as permethrin, cypermethrin, zetacypermethrin, and bifenthrin, than were previously available in solvents suitable for the preparation of emulsifiable concentrates for agricultural, domestic, and horticultural use. The solvent combination has the added advantage of low odor, low viscosity at reduced temperatures, and a high flash point. The use of this combination of solvents to provide concentrated solutions of pesticides is heretofore unknown. Compositions of the same solvents are also useful for the preparation of microemulsions of pesticides.

SUMMARY OF INVENTION

For the purposes of this application an emulsifiable concentrate (EC) formulation is a concentrated solution of a pesticide in an organic solvent that contains suitable surfactants, including emulsifiers, so that when mixed with a relatively large volume of water it will give a stable oil-in-water emulsion for application, as by spraying, to the target site. The requirements for a satisfactory EC formulation are: chemical stability (no loss of active ingredient during storage); physical stability (no phase separation over the range of temperatures likely to be encountered during storage); high flashpoint (for safe warehouse storage); and low viscosity (for ease of mixing with water for application). If the formulation is to be used or marketed in the United States, it is essential that it be accepted for registration by the Environmental Protection Agency (EPA).

For the purposes of this application a microemulsion (ME) formulation is an emulsion of a small amount of a pesticide solution in an organic solvent in a relatively large volume of water, yielding a concentration of the pesticide ready for application to the target site. The microemulsion will be formed through the use of suitable surfactants, including an amount of emulsifier substantially greater relative to the amount of pesticide than in EC formulations. The resulting emulsion droplets are so small that the microemulsion formulation is optically clear, rather than milky in appearance. Some microemulsions, although ready for use as prepared, retain microemulsion characteristics such as optical clarity upon further dilution with water. The requirements for a satisfactory ME formulation are chemical and physical stability. Again, registration with the Environmental Protection Agency (EPA) is essential, if the formulation is to be used or marketed in the United States.

The studies that led to the development of the novel combination of solvents of this invention were motivated by the desire to improve EPA-approved emulsifiable concentrates containing e.g. from 2 to 3.2 pounds of pyrethroid per gallon of formulation. While these products have been marketed and used successfully, at the low temperatures encountered in some storage facilities the EC formulations undergoes phase separation, including the formation of crystals.

A number of solvents and solvent combinations were investigated for solving the storage stability problem noted above, but a combination of three solvents has now been found to provide excellent results. The three solvents used in this combination are:

- glyceryl triacetate, available from Eastman Chemical Products, Inc. as Kodaflex® Triacetin Plasticizer (hereafter called Triacetin);
- a hydrotreated light petroleum distillate consisting predominantly of $C_{12}$ to $C_{15}$ isoparafinic hydrocarbons available e.g. from Exxon Company as Isopar M (hereafter called Isopar M);
- bis(-methylethyl)-1,1'-biphenyl available from Ridge Technologies, Inc. as NuSOlv™ ABP-103, (hereafter called ABP-103).

The preferred solvent system is made up of 15 to 32 wt. % Triacetin, 15 to 32 wt. % Isopar M, and 40 to 55 wt. % ABP-103.

BRIEF DESCRIPTION OF THE FIGURE

A triangular experimental design diagram for a three component blend.

Figure 1:
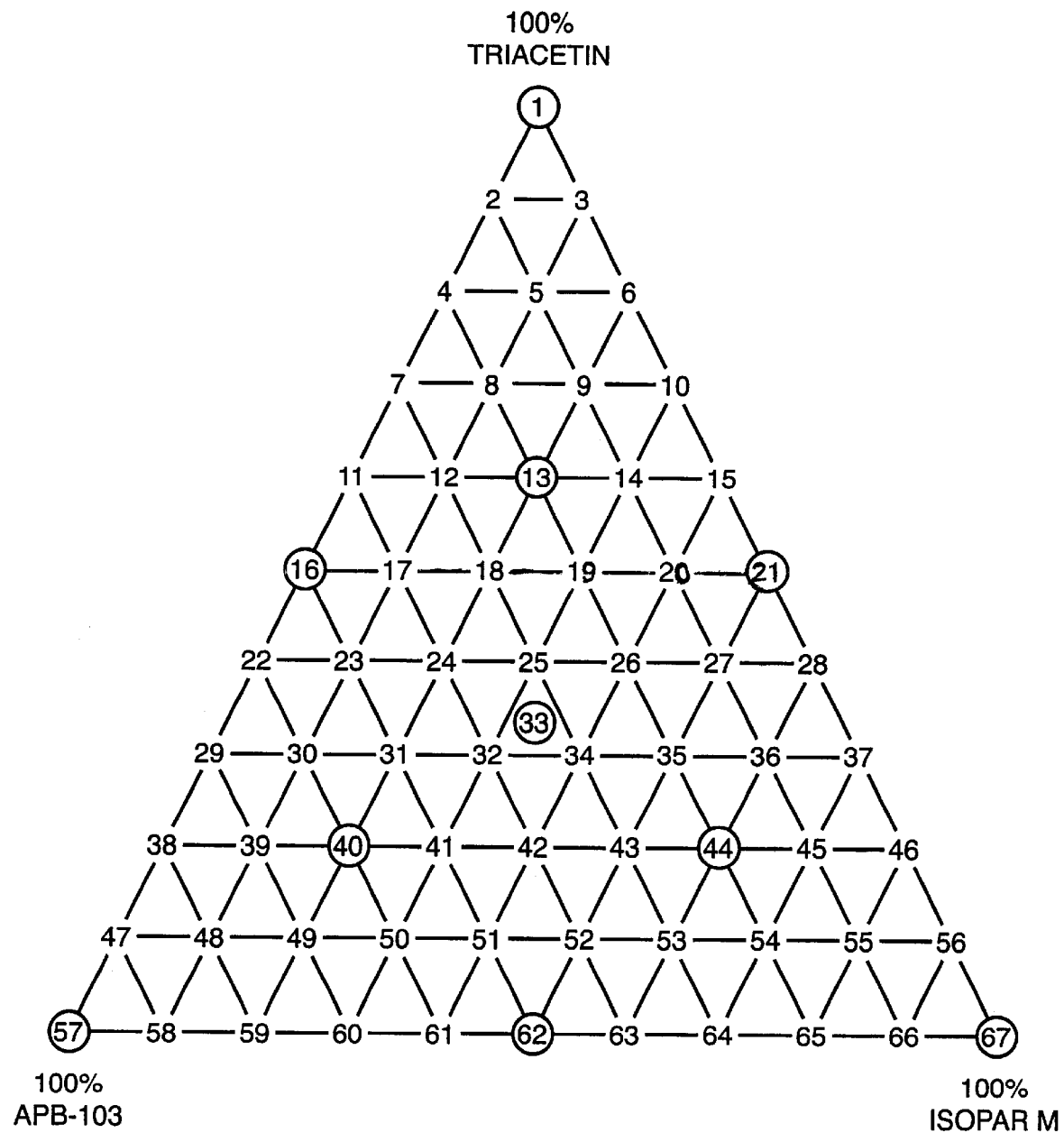
FIG. 1, represents the solvent compositions in which the performance of pesticide products with changes in solvent ratios were evaluated.

Each numbered point along the side of the triangle represents a ten weight percent increase in one of the two components and a ten weight percent decrease in the other. Solvent blends were prepared with compositions corresponding to the circled points as follows:

| Point No. | Triacetin | Isopar M | ABP-103 |
|---|---|---|---|
| 1. | 1 | 100 | — | — |
| 2. | 13 | 60 | 20 | 20 |
| 3. | 16 | 50 | — | 50 |
| 4. | 21 | 50 | 50 | — |
| 5. | 33 | 33.3 | 33.3 | 33.3 |
| 6. | 40 | 20 | 20 | 60 |
| 7. | 44 | 20 | 60 | 20 |
| 8. | 57 | — | — | 100 |
| 9. | 62 | — | 50 | 50 |
| 10. | 67 | — | 100 | — |

A 27.0% wt./wt. formulation (approximately 2 lb/gal concentration) of bifenthrin was prepared in each of the ten solvent combinations listed above, with the results shown in Table 1.

TABLE 1

Studies for a 2 lb/gal Bifenthrin EC

| Point No. | Solvent A Wt. % | Solvent B Wt. % | Solvent C Wt. % | Specific Gravity, g/mL | Appearance | Viscosity cps |
|---|---|---|---|---|---|---|
| 1 | 100 | — | — | 1.166 | crystallized | — |
| 13 | 60 | 20 | 20 | — | phase sep. | — |
| 16 | 50 | — | 50 | 1.084 | solution | 200 |
| 21 | 50 | 50 | — | — | phase sep. | — |
| 33 | 33.3 | 33.3 | 33.3 | — | phase sep. | — |
| 40 | 20 | 20 | 60 | 1.006 | solution | 80 |
| 44 | 20 | 60 | 20 | — | phase sep. | — |
| 57 | — | — | 100 | 1.015 | solution | 200 |
| 62 | — | 50 | 50 | — | crystallized | — |
| 67 | — | 100 | — | — | crystallized | — |

Properties of a 27% W/W Bifenthrin Solution at 36° F.

Solvent A is Triacetin
Solvent B is Isopar M
Solvent C is ABP-103
phase sep. means phase separation It is clear that the addition of Isopar M to the solvent blend of Triacetin and ABP-103 lowers the viscosity of the solvent system. However, bifenthrin is not sufficiently soluble in Isopar M that a 2 lb/gal EC formulation of bifenthrin can be prepared in Isopar M alone. Of the solvent blends tested, the most promising performance was the 20/20/60 blend represented by point number 40. The next step was to investigate the solubility of bifenthrin in blends close to the blend of point 40, viz., points 18, 24, 25, 31, 32, 34, 41, 42, 49, 50, 51, 52, 59, 60, 61, and 63. Points to the left of point 40 were not considered, since the evaluation shown in Table 1 indicated that blends consisting predominantly of Triacetin and ABP-103 would result in high viscosity. The results for these blends are given in Table 2.

TABLE 2

Further Studies for a 2 lb/gal Bifenthrin EC

| Point No. | Solvent | | | Appearance of a 27% W/W Bifenthrin Solution | |
|---|---|---|---|---|---|
| | A Wt. % | B Wt. % | C Wt. % | at 36° F. | at 1° F. |
| 18 | 50 | 20 | 30 | phase sep. | phase sep. |
| 24 | 40 | 20 | 40 | phase sep. | phase sep. |
| 25 | 40 | 30 | 30 | phase sep. | phase sep. |
| 31 | 30 | 20 | 50 | solution | solution |
| 32 | 30 | 30 | 40 | phase sep. | phase sep. |
| 34 | 30 | 40 | 30 | phase sep. | phase sep. |
| 40 | 20 | 20 | 60 | solution | phase sep. |
| 41 | 20 | 30 | 50 | solution | phase sep. |
| 42 | 20 | 40 | 40 | phase sep. | phase sep. |
| 49 | 10 | 20 | 70 | solution | phase sep. |
| 50 | 10 | 30 | 60 | solution | phase sep. |
| 51 | 10 | 40 | 50 | solution | phase sep. |
| 52 | 10 | 50 | 40 | crystallized | crystallized |
| 59 | — | 20 | 80 | solution | phase sep. |
| 60 | — | 30 | 70 | solution | phase sep. |
| 61 | — | 40 | 60 | crystallized | crystallized |
| 62 | — | 50 | 50 | crystallized | crystallized |
| 63 | — | 60 | 40 | crystallized | crystallized |

Solvent A is Triacetin
Solvent B is Isopar M
Solvent C is ABP-103
phase sep. means phase separation The blends discussed above have been prepared without the surfactants necessary to form emulsions when the EC's are diluted with water for use in the field. For the preparation of formulations suitable for use as EC's, 8.50% wt/wt surfactants have been added to the selected solvent blend (point 31).

The composition of the resulting Bifenthrin 2 EC is:

| Ingredient | % wt/wt |
|---|---|
| Bifenthrin (93.5%) | 25.06 |
| Phenylsulfonate CA[1] | 3.00 |
| Igepal CO-530[2] | 5.50 |
| Triacetin | 20.02 |
| Isopar M | 13.05 |
| ABP-103 | 33.37 |

[1]from Hoechst Celanese Specialty Chemicals Group
[2] an alkyl phenol ethoxylate Rhone-Poulenc Those skilled in the art will recognize that there are a great number of surfactants of various structures commercially available, many of which, either singly or in combination, may be satisfactorily used in the EC's based on the solvent system of this invention.

Similarly to the preparation of the bifenthrin EC formulation described above, a 27.0% wt./wt. formulation (approximately 2 lb/gal concentration) of cypermethrin was prepared in each of the ten solvent combinations listed above, with the results shown in Table 3.

TABLE 3

Properties of a 27% W/W Cypermethrin Solution at 36° F.

| Point No. | Solvent | | | Specific Gravity, g/mL | Appearance | Viscosity cps |
|---|---|---|---|---|---|---|
| | A Wt. % | B Wt. % | C Wt. % | | | |
| 1 | 100 | — | — | 1.172 | solution | 200 |
| 13 | 60 | 20 | 20 | — | phase sep. | — |
| 16 | 50 | — | 50 | 1.089 | solution | 220 |
| 21 | 50 | 50 | — | — | phase sep. | — |
| 33 | 33.3 | 33.3 | 33.3 | — | phase sep. | — |
| 40 | 20 | 20 | 60 | 1.010 | solution | 100 |
| 44 | 20 | 60 | 20 | — | phase sep. | — |
| 57 | — | — | 100 | 1.018 | solution | 260 |
| 62 | — | 50 | 50 | 0.940 | solution | 60 |
| 67 | — | 100 | — | — | phase sep. | — |

Solvent A is Triacetin
Solvent B is Isopar M
Solvent C is ABP-103
phase sep. means phase separation Cypermethrin showed solvent system interactions similar to those shown by bifenthrin in terms of viscosity, specific gravity, and physical appearance at 36° F. The main difference was the greater solubility of cypermethrin.

Here, too, point 40 appeared most promising and based on the evaluations in Table 2, the composition corresponding to point 31 was selected as having the most satisfactory characteristics. (The blend corresponding to point 60 had a lower viscosity, but at 1° F. it showed phase separation. The blend corresponding to point 40 did not.)

The composition of the resulting Cypermethrin 2 EC is:

| Ingredient | % wt/wt |
|---|---|
| Cypermethrin (93.5%) | 24.96 |
| Phenylsulfonate CA[1] | 3.00 |
| Igepal CO-430[2] | 2.20 |
| Tergitol XD[3] | 3.30 |
| Triacetin | 20.09 |
| Isopar M | 13.05 |
| ABP-103 | 33.40 |

[1]from Hoechst Celanese Specialty Chemicals Group
[2]an alkyl phenol ethoxylate from Rhone-Poulenc
[3]a secondary alkyl ethoxylate from Stepan Co.

In the same manner as described above, a 43.6% wt./wt. formulation (approximately 4 lb/gal concentration) of permethrin was prepared in each of the ten blends, with the results shown in Table 4.

TABLE 4

Properties of a 43.6% W/W Permethrin Solution at 36° F.

| | Solvent | | | Specific Gravity, g/mL | Appearance | Viscosity cps |
|---|---|---|---|---|---|---|
| | A Wt. % | B Wt. % | C Wt. % | | | |
| 1 | 100 | — | — | 1.179 | solution | 200 |
| 13 | 60 | 20 | 20 | — | phase sep. | — |
| 16 | 50 | — | 50 | 1.110 | solution | 220 |

TABLE 4-continued

| | Solvent | | | Properties of a 43.6% W/W Permethrin Solution at 36° F. | | |
|---|---|---|---|---|---|---|
| A Wt. % | B Wt. % | C Wt. % | Specific Gravity, g/mL | Appearance | Viscosity cps |
| 21 | 50 | 50 | — | — | phase sep. | — |
| 33 | 33.3 | 33.3 | 33.3 | 1.041 | solution | 80 |
| 40 | 20 | 20 | 60 | 1.045 | solution | 140 |
| 44 | 20 | 60 | 20 | — | phase sep. | — |
| 57 | — | — | 100 | 1.052 | solution | 220 |
| 62 | — | 50 | 50 | — | crystallized | — |
| 67 | — | 100 | — | — | crystallized. | — |

Solvent A is Triacetin
Solvent B is Isopar M
Solvent C is ABP-103
phase sep. means phase separation The physical properties of the permethrin blends follow the same general pattern as shown by the other two active ingredients. Again, the main difference is in the solubility of permethrin.

As a practical matter the permethrin formulation selected must be a 36.8% wt/wt concentration corresponding to the 3.2 lb/gal EC registered with the EPA. In order to satisfy this requirement, it is necessary for the permethrin 3.2 EC to have a specific gravity of 1.045 gm/mL. This places a restriction on the possible solvent ratios that may be used. The solvent ratios that would meet the specific gravity requirement were plotted on the experimental design triangle, formulated, and evaluated for physical stability (phase separation) at 1° F.

The composition of the Permethrin 3.2 EC meeting these conditions is:

| Ingredient | % wt/wt |
|---|---|
| Permethrin (94.5%) | 38.99 |
| Phenylsulfonate CA[1] | 3.00 |
| Igepal CO-530[2] | 4.95 |
| Tergitol XD[3] | 0.55 |
| Triacetin | 11.46 |
| Isopar M | 14.05 |
| ABP-103 | 27.00 |

[1]from Hoechst Celanese Specialty Chemicals Group
[2]an alkyl phenol ethoxylate from Rhone-Poulenc
[3]a secondary alkyl ethoxylate from Stepan Co.

It is clear that higher concentrations of permethrin may be successfully prepared in the solvent system of the invention.

The preparation of the EC and ME formulations in the solvent system of this invention are described in detail in the following examples.

EXAMPLE 1

Preparation of a 2 Lb/gal Emulsifiable Concentrate Formulation of Bifenthrin

To a 1000 mL beaker is added 334.0 grams (33.4 wt. %) of ABP-103, followed by 188.3 grams (18.83 wt. %) of Triacetin, and then 130.5 grams (13.05 wt. %) of Isopar M. To this mixture is added 262.2 grams (26.22 wt. %) of 89% bifenthrin technical material, followed by 33.0 grams (3.30 wt. %) of Niagara 3[a], Tergitol XD[b], or Toximol 8320[c], then 30.0 grams (3.00 wt. %) of phenylsulfonate CA[d], and finally 22.0 grams (2.20 wt. %) of Igepal CO-430[e],. Upon completion of the addition the entire formulation is vigorously mixed with a propeller type mixer until the mixture becomes uniform.

[a]an emulsifying agent consisting of a nonionic paste of 100% polyalkylene glycol ether sold by Union Carbide Chemical and Plastics Co.
[b]a secondary alkyl ethoxylate sold by Stepan Co.
[c]a blend of anionic calcium salts and nonionics sold by Stepan Co.
[d]a proprietary surfactant sold by Hoechst Celanese Specialty Chemicals Group.
[e]an alkyl phenol ethoxylate sold by Rhone-Poulenc.

EC's prepared in this manner have demonstrated excellent storage stability and upon dilution with water in the field readily yielded stable emulsions for application.

EXAMPLE 2

Preparation of 3.2 Lb/gal Emulsifiable Concentrate Formulation of Permethrin

To a 1000 mL beaker is added 53.19 grams (53.19 wt. %) of a pre-blended mixture consisting of 50% wt. % ABP-103, 20% wt. % Triacetin, and 30 wt. % Isopar M. To this pre-blended mixture is added 38.31 grams (38.31 wt. %) of 95.8% permethrin technical material, followed by 8.50 grams (8.50 wt. %) of Agent X1810-49[f]. Upon completion of the addition the entire formulation is vigorously mixed with a propeller type mixer until the mixture becomes uniform.

[f]a proprietary blend of emulsifiers sold by Stepan Co.

EC's prepared in this manner have demonstrated excellent storage stability and upon dilution with water in the field readily yielded stable emulsions for application.

EXAMPLE 3

Preparation of 0.025% Bifenthrin Microemulsion Formulation

Step A Preparation of a 13% wt. % Bifenthrin Manufacturing Use Product (MUP)

To a mixing tank is added 29.94 grams (59.89 wt. %) of ABP-103, followed by 10.06 grams (20.12 wt. %) of Triacetin, and then 3.08 grams (6.16 wt. %) of Isopar M. The resulting blend is stirred until uniform, and then 6.92 grams (13.83 wt. %) of 94% bifenthrin technical material is added. (The rate of solubility can be significantly accelerated when the bifenthrin is added as a molten liquid rather than as a solid, but either form is sufficient.) Upon completion of the addition the entire formulation is vigorously mixed with a propeller type mixer until the mixture becomes uniform.

Step B Preparation of 0.025% Bifenthrin Microemulsion Formulation

To a mixing tank are added 30.73 grams (0.192 wt. %) of a 13% wt. % MUP as prepared in Step A and 26.56 grams (0.166 wt. %) of Berol 927[g]. Upon completion of the addition the mixture is mixed until uniform and then 15,938.40 grams (99.615 wt. %) of deionized water is added. The resulting mixture is mixed until uniform and 4.32 grams (0.027 wt. %) of Legend MK[h] is added. Upon completion of the addition the entire formulation is vigorously mixed with a propeller type mixer until the mixture becomes uniform.

[g]an emulsifying agent consisting of a blend of anionic calcium salts and nonionics sold by Berol Nobel, Nobel Industries.
[h]an antimicrobial biocide sold by Rohm and Haas Co.

ME's prepared in this manner have demonstrated excellent storage stability.

Representative formulations that can be prepared by the methods exemplified above include:

| Bifenthrin 0.25% ME | | Zetacypermethrin 1.5 EC | |
|---|---|---|---|
| Ingredient | Wt/Wt% | Ingredient | Wt/Wt% |
| Bifenthrin (94%) | 0.053 | Zetacypermethrin | 21.35 |
| ABP 103 | 0.23 | ABP 103 | 36.82 |
| Triacetin | 0.077 | Triacetin | 20.02 |
| Isopar M | 0.024 | Isopar M | 13.31 |
| Legend Mk | 0.027 | Phenylsulfonate CA | 3.00 |
| Berol 927 | 0.0332 | Igepal 430 | 2.75 |
| Water | 99.257 | Tergitol XD | 2.75 |

It is apparent that various modifications may be made in the formulations in the solvent system of this invention without departing from the inventive concepts as defined in the following claims.

What is claimed is:

1. A solution of bifenthrin in a solvent system consisting essentially of 15 to 33 wt. % glyceryl triacetate (Solvent A), 15 to 33 wt. % hydrotreated light petroleum distillate having a major proportion of $C_{12}$ to $C_{15}$ isoparafinic hydrocarbons (Solvent B), 40 to 55 wt. % bis(-methylethyl)-1,1'-biphenyl (Solvent C) and about 8.5 wt. % of one or more surfactants, the content of said bifenthrin being about 23.4 wt. % and the ratio of Solvents A:B:C being about 30:20:50.

2. A solution of permethrin in a solvent system consisting essentially of 15 to 33 wt. % glyceryl triacetate (Solvent A), 15 to 33 wt. % hydrotreated light petroleum distillate having a major proportion of $C_{12}$ to $C_{15}$ isoparafinic hydrocarbons (Solvent B), 40 to 55 wt. % bis(-methylethyl)-1,1'-biphenyl (Solvent C) and about 8.5 wt. % of one or more surfactants, the content of said permethrin being about 36.8 wt. % and the ratio of Solvents A:B:C being about 22:27:51.

3. A solution of cypermethrin in a solvent system consisting essentially of 15 to 33 wt. % glyceryl triacetate (Solvent A), 15 to 33 wt. % hydrotreated light petroleum distillate having a major proportion of $C_{12}$ to $C_{15}$ isoparafinic hydrocarbons (Solvent B), 40 to 55 wt. % bis(-methylethyl)-1,1'-biphenyl (Solvent C) and about 8.5 wt. % of one or more surfactants, the content of said cypermethrin being about 23.3 wt. % and the ratio of Solvents A:B:C being about 30:20:50.

4. A solution of zetacypermethrin in a solvent system consisting essentially of 15 to 33 wt. % glyceryl triacetate (Solvent A), 15 to 33 wt. % hydrotreated light petroleum distillate having a major proportion of $C_{12}$ to $C_{15}$ isoparafinic hydrocarbons (Solvent B), 40 to 55 wt. % bis(-methylethyl)-1,1'-biphenyl (Solvent C) and about 8.5 wt. % of one or more surfactants, the content of said zetacypermethrin being about 21.35 wt. % and the ratio of Solvents A:B:C being about 29:19:52.

5. A solution of a pesticide in a solvent system, said solvent system consisting essentially of glyceryl triacetate, hydrotreated light petroleum distillate having a major portion of $C_{12}$ to $C_{15}$ isoparafinic hydrocarbons, and bis(-methylethyl)-1,1'-biphenyl and wherein said pesticide is selected from the group consisting of alphacypermethrin, bifenthrin, carbosulfan, clomazone, cypermethrin, permetlrin, and zetacypermethrn.

6. A pesticidal formulation comprising a solution of a pesticide in a solvent system and up to 15 wt. % of one or more surfactants; wherein said solvent system consists essentially of glyceryl triacetate, hydrotreated light petroleum distillate having a major portion of $C_{12}$ to $C_{15}$ isoparafinic hydrocarbons, and bis(-methylethyl)-1,1'-biphenyl and said pesticide is selected from the group consisting of alphacypermethrin, bifenthrin, carbosulfan, clomazone, cypermethrin, permethrin, and zetacypermethrin.

7. An emulsion comprising a pesticide concentrate, deionized water, and at least one surfactant, wherein said pesticide concentrate comprises glyceryl triacetate, hydrotreated light petroleum distillate having a major portion of $C_{12}$ to $C_{15}$ isoparafinic hydrocarbons, bis(-methylethyl)-1,1'-biphenyl, and a pesticide; said pesticide being selected from the group consisting of alphacypermethrin, bifenthrin, carbosulfan, clomazone, cypermethrin, permethrin, and zetacypermethrin.

8. A solution of permethrin in a solvent system comprising about 36.8 wt. % permethrin and said solvent system containing: (i) about 10 to about 20 wt. % of glyceryl triacetate, (ii) about 14.05 wt. % of hydrotreated light petroleum distillate having a major proportion of $C_{12}$ to $C_{15}$ isoparafinic hydrocarbons, (iii) about 27 wt. % of bis(-methylethyl)-1,1'-biphenyl, and (iv) about 8.5 wt. % of one or more sulfactants.

* * * * *